United States Patent [19]

Cooper

[11] Patent Number: 5,371,253
[45] Date of Patent: Dec. 6, 1994

[54] PROCESS FOR PRODUCING ESTERIFIED ALKOXYLATED MONOGLYCERIDES AND DIGLYCERIDES

[75] Inventor: Charles F. Cooper, Paoli, Pa.

[73] Assignee: Arco Chemical Technology, L.P., Wilmington, Del.

[21] Appl. No.: 168,546

[22] Filed: Dec. 14, 1993

[51] Int. Cl.$^5$ ............................................. C07C 51/00
[52] U.S. Cl. .................................. 554/173; 554/149;
554/168; 554/172; 568/613; 568/616; 568/623
[58] Field of Search ............... 554/168, 149, 173, 172;
568/613, 616, 628

[56] References Cited

U.S. PATENT DOCUMENTS

| 4,861,613 | 8/1989 | White et al. | 426/611 |
| 5,118,448 | 6/1992 | Cooper | 554/168 |
| 5,135,683 | 8/1992 | Cooper | 554/151 |
| 5,266,346 | 11/1993 | Klemann et al. | 426/611 |

FOREIGN PATENT DOCUMENTS

| 0352819 | 1/1990 | European Pat. Off. |
| 0481523 | 4/1992 | European Pat. Off. |

OTHER PUBLICATIONS

Applied Catalysis, 8(1983) 57–70, Elsevier Science Publishers B.V., Amsterdam–Andrew T. Guttmann & Robert K. Grasselli.
Tetrahedron Letters No. 49, pp. 4269–4270, 1970 Synthesis of Esters via Aleyl.Tert.-Butyl Ethers.

*Primary Examiner*—José G. Dees
*Assistant Examiner*—Deborah D. Carr
*Attorney, Agent, or Firm*—Stephen D. Harper

[57] ABSTRACT

Esterified alkoxylated mono- and diglycerides suitable for use as reduced calorie fat substitutes in food products may be produced by alkoxylating a tertiary alkyl partial ether of glycerin with an epoxide and then reacting the alkoxylated glycerin tertiary alkyl partial ether thereby obtained with a fatty acid under acid-catalyzed conditions. Separate deprotection and esterification steps are not required, resulting in a considerably streamlined process as compared to alternative methods of synthesizing alkoxylated fat substitutes having one or two fatty acid acyl groups attached directly to glycerin.

21 Claims, No Drawings

PROCESS FOR PRODUCING ESTERIFIED ALKOXYLATED MONOGLYCERIDES AND DIGLYCERIDES

FIELD OF THE INVENTION

This invention pertains to methods for the preparation of useful esterified alkoxylated glycerins wherein one or two fatty acid acyl groups are connected directly to the glyceryl residue and at least one other fatty acid acyl group is connected to the glyceryl residue through an oxyalkylene segment.

BACKGROUND OF THE INVENTION

Esterified alkoxylated glycerin and other esterified alkoxylated polyols have recently been identified as useful reduced calorie fat substitutes. Compounds of this type, which are described more fully in U.S. Pat. No. 4,861,613, are substantially resistant to hydrolysis upon ingestion owing to the high proportion of linkages in which the carbons adjacent to oxygen in the fatty acid ester groups are secondary or tertiary in structure. In a preferred embodiment of such substances, the structure may be represented as follows:

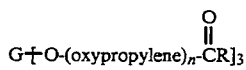

$$G \!\!-\!\![O\text{-(oxypropylene)}_n\text{-CR}]_3$$
(with C=O)

wherein G is a glyceryl radical, n is from about 1 to 5 on average, and R is a long chain paraffinic or olefinic hydrocarbon radical derived from a fatty acid.

However, the ability to use esterified alkoxylated polyols of this type at relatively high concentrations in food compositions is somewhat limited by the pronounced resistance of such substances to digestion. Since the esterified alkoxylated polyols are hydrolyzed and absorbed to only a very limited degree, the liquid versions of such substances tend to retain their oil-like physical characteristics after ingestion. Consumption of large amounts of these fat substitutes can result in leakage of the fat substitutes through the anal sphincter and separation of the fat substitute as an oil from the excreted fecal matter.

To enhance the acceptability of fat substitutes of this type, modified esterified alkoxylated glycerins have been developed which are somewhat less resistant to enzymatic hydrolysis than previously known esterified alkoxylated glycerins and yet still have significantly reduced calorie availability as compared to a conventional fully digestible triglyceride lipid. These modified esterified alkoxylated glycerins have at least one fatty acid acyl group attached directly to the glyceryl radical. These directly-attached acyl groups are readily hydrolyzed upon ingestion, rendering the compound less fat-like in character owing to the loss of one or two long-chain fatty acid acyl groups.

The other acyl groups in the esterified alkoxylated glycerin are attached to the glyceryl radical through oxyalkylene segments and thus are resistant towards enzymatic hydrolysis. Esterified alkoxylated monoglycerides and diglycerides of this type and their utility as reduced calorie fat mimetics are described more fully in European Patent Publication No. 481,523, incorporated herein by reference in its entirety.

The selective synthesis of esterified alkoxylated mono- and diglycerides is not straightforward. While procedures for obtaining such substances using ketal or benzyl protecting groups to selectively direct the addition of epoxide to the glycerin prior to esterification have been described, most notably in U.S. Pat. Nos. 5,118,448 and 5,135,683 (incorporated herein by reference in their entirety), such methods are not ideally suited for commercial purposes since in each instance separate steps are required for removal of the protective groups and esterification. For a fat substitute to penetrate the potential market for such food ingredients to the greatest extent, it must be capable of being produced at a minimum premium in cost over fully digestible vegetable and animal lipids. It is well-known that additional processing steps can significantly increase the expense of manufacturing food additives. Thus, a great need still exists for improved processes whereby an esterified alkoxylated glycerin having at least one acyl group attached directly to the glyceryl residue may be readily and economically prepared.

SUMMARY OF THE INVENTION

This invention provides a process for producing an esterified alkoxylated glycerin having from one to two fatty acid acyl groups attached directly to glycerin comprising the steps of (a) reacting a tertiary alkyl partial ether of glycerin with a $C_2$–$C_6$ aliphatic epoxide in the presence of a basic catalyst to form an alkoxylated glycerin tertiary alkyl partial ether and (b) reacting the alkoxylated glycerin tertiary alkyl partial ether with a fatty acid in the presence of an acidic catalyst at a temperature effective to form the esterified alkoxylated glycerin, water, and a tertiary olefin. The process offers the considerable practical advantage of simultaneously accomplishing both removal of the tertiary alkyl protecting groups and esterification of the alkoxylated glycerin, yet also furnishes a high yield of esterified alkoxylated glycerin requiring minimal additional processing to render it suitable for use as a fat substitute due to the lack of significant by-product formation and product decomposition.

The process of this invention may also be practiced as an integrated scheme wherein a triglyceride is hydrolyzed to provide both the glycerin and the fatty acid to be utilized and the tertiary olefin that has been reacted with glycerin is recovered following conversion of the alkoxylated glycerin tertiary alkyl partial ether and reused in subsequent cycles.

DETAILED DESCRIPTION OF THE INVENTION

The process of this invention requires the use of a tertiary alkyl partial ether of glycerin having at least one and at most two hydroxyl groups and at least one and at most two tertiary alkyl ether groups. Such substances may thus correspond to the general structure $(HO)_x$—G—$(O-R)_y$ wherein x is 1 or 2, y is 1 or 2, the sum of x+y is 3, G is a glyceryl residue

$(CH_2CHCH_2)$, and R is tertiary butyl or tertiary amyl. To prepare an esterified alkoxylated monoglyceride, the value of y should be equal to 1 and the value of x should be equal to 2. Similarly, y should be equal to 2 and x should be equal to 1 if an esterified alkoxylated diglyceride is desired. Mixtures of different tertiary alkyl partial ethers may be employed, if desired. While the position of the tertiary alkyl ether group or groups on the glyceryl residue is not critical, the properties of the resulting fat substitute may be advantageously controlled by selecting specific positional isomers for use if so desired. The tertiary alkyl ether group may thus be attached at the center (2) or end (1 or 3) carbon atoms of the glyceryl residue where y=1; if two such groups are present, they may be substituted on the 1 and 2 or the 1 and 3 carbon atoms of the glyceryl residue.

Tertiary alkyl partial ethers of glycerin may be prepared by any suitable method. Such methods are well-known in the art and include the acid-catalyzed etherification of glycerin with a tertiary olefin such as isobutylene or isoamylene. A tertiary alcohol such as t-butyl alcohol or t-amyl alcohol may also be utilized as a reactant in place of the tertiary olefin. Specific procedures for obtaining tertiary alkyl partial ethers of glycerin may be found, for example, in U.S. Pat. No. 1,968,033 (Evans et al.) and Czech. Pat. Doc. No. 190,755, the teachings of which are incorporated herein by reference in their entirety. Preferably, the tertiary olefin contains from 4 to 5 carbon atoms. The use of a mixture of mono- and dialkyl ethers of glycerin in the process of this invention is particularly advantageous since the need to perform a tedious separation of such compounds from the mixed reaction product typically obtained by reaction of glycerin with a tertiary olefin is thereby eliminated. The molar ratio of glycerin:tertiary olefin is preferably from 1:0.9 to 1:2.2. Unreacted glycerin as well as the triether of glycerin may also be present in minor proportions (e.g., up to about 25 mole % of each) without significant adverse effect. The unreacted glycerin will be converted during the process of the invention to an esterified alkoxylated polyol of the type described in U.S. Pat. No. 4,861,613 while the triether of glycerin will be transformed to a mono-, di-, or triglyceride in the esterification step. Such co-products may be utilized to advantage as components of a reduced calorie fat substitute; fractionation of the reaction product obtained following esterification thus is not necessary.

The tertiary alkyl partial ether of glycerin is reacted with a $C_2$—$C_6$ aliphatic epoxide in the presence of a basic catalyst to form an alkoxylated glycerin tertiary alkyl partial ether. Methods of alkoxylating alkyl ethers of glycerin are known in the art and are described, for example, in U.S. Pat. Nos. 2,932,670 (Blake), 2,932,616 (Blake), and 4,241,224 (Newkirk et al.). The teachings of these patents are incorporated herein by reference in their entirety. During the alkoxylation step, the hydroxy group or groups on the tertiary alkyl partial ether of glycerin participate in a nucleophilic ring-opening of the aliphatic epoxide so as to add an oxyalkylene unit onto the partial ether. Additional equivalents of epoxide can further react with the hydroxy group of the initially added oxyalkylene unit so as to form polymeric oxyalkylene segments. The tertiary alkylether groups on the glycerin function so as to protect or mask one or two of the three hydroxy groups potentially available for reaction on the glycerin. Propylene oxide is the most preferred epoxide, but other suitable $C_2$-$C_6$ aliphatic epoxides include ethylene oxide, 1,2 butene oxide, isobutylene oxide, 2,3-butene oxide (cis and/or trans), 1,2-pentene oxide, 2,3-pentene oxide, cyclopentene oxide, 1,2-hexene oxide, cyclohexene oxide, methyl glycidyl ether, ethyl glycidyl ether, and the like may also be used, however. Mixtures of epoxides may be employed. If more than one type of epoxide is used, it may be desirable to add the different epoxides sequentially so as to vary the location of the different oxyalkylene units within the end products. While the relative amounts of epoxide and tertiary alkyl partial ether utilized are not critical, preferably the molar ratio of epoxide to ether is from 1:1 to 20:1. More preferably, the molar ratio is from X:1 to 10X:1, wherein X is equal to the number of free hydroxyl groups on the tertiary alkyl partial ether of glycerin.

In a preferred embodiment of this invention, the alkoxylated glycerin tertiary alkyl partial ether produced has the general structure

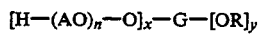

$$[H-(AO)_n-O]_x-G-[OR]_y$$

wherein R is tertiary butyl or tertiary amyl, G is a glyceryl residue, X is 1 or 2, Y is 1 or 2, the sum of X+Y is 3, n is from 1 to 10, and AO is an oxyalkylene unit derived from the epoxide (preferably, oxyethylene, oxypropylene, oxybutylene, or a combination thereof).

It has been found that the tertiary alkyl ether functionality of the tertiary alkyl partial ether of glycerin is inert under the alkoxylation conditions of this process. No oxyalkylene groups are inserted between the glyceryl radical and the tertiary alkyl ether group, in contrast to the transesterification and oxyalkylene insertion observed when an ester group is attached directly to the glycerin. The use of a basic catalyst for alkoxylation is essential to the successful operation of the present process since an acidic catalyst may lead to the premature loss of the protective tertiary alkyl ether groups and the introduction of oxyalkylene units at all three positions of the glyceryl residue. The basic catalyst may preferably be selected from the group consisting of basic alkali metal compounds, basic alkaline earth compounds, and basic tertiary amines. Suitable alkali metal and alkaline earth catalysts include the hydrides, carbonates, oxides, hydroxides, carboxylates, alkoxides, and sulfates of lithium, sodium, potassium, barium, calcium, and strontium as well as the elemental forms of the metals (e.g., sodium or potassium metal dispersions). Generally speaking, it is desirable to pre-react the tertiary alkyl partial ether of glycerin with the alkali metal or alkaline earth catalyst to form the salt (alkoxide) of the tertiary alkyl partial ether prior to reaction with the epoxide. For example, if sodium hydroxide or potassium hydroxide is employed as the catalyst, a mixture of the tertiary alkyl partial ether and catalyst may be heated under conditions such that the water formed by reaction of the components is removed and the alkali metal salt of the tertiary alkyl partial ether is generated.

Suitable tertiary amines for use in this process include aliphatic, aromatic, and mixed aliphatic-aromatic amines such as triethylamine, N,N-dialkyl anilines, dimethylaminocyclohexane, tri-n-propylamine, tetraethyl ethylenediamine, N,N'-dialkylpiperazines, N-alkyl pyrrolidinones, quinuclidine, and the like.

The amount of basic catalyst employed must be sufficient to effectively catalyze the addition of the epoxide to the hydroxyl group(s) of the tertiary alkyl partial ether of glycerin. Preferably this amount is from about 0.001 to 1 equivalent of basic catalyst per equivalent of hydroxyl groups in the tertiary alkyl partial ether. The epoxide and tertiary alkyl partial ether are preferably reacted at a temperature of from 50° C. to 150° C. for a time effective to accomplish substantial (e.g., over 75%) conversion of the epoxide. Reaction times of from 1 to 48 hours will typically suffice. The molar ratio of epoxide to tertiary alkyl partial ether may be varied as desired depending upon the degree of alkoxylation desired in the final esterified alkoxylated polyol, but generally from about 1 to 25 (more preferably, 1 to 10) equivalents of epoxide per equivalent of hydroxyl groups in the tertiary alkyl partial ether will be typically employed. It is generally desirable to add the epoxide incrementally with agitation to the tertiary alkyl partial ether and basic catalyst. The alkoxylation may be carried out in the presence of an inert organic solvent. When the desired degree of epoxide conversion has been achieved, the alkoxylated glycerin tertiary alkyl partial ether may be purified by removing any unreacted epoxide by a suitable method such as vacuum stripping. The alkoxylated glycerin tertiary alkyl partial ether may also be treated to remove or neutralize the residual basic catalyst. Methods such as filtration, extraction, precipitation, or absorption can be used depending on the particular catalyst employed. Any of the standard methods for removing a basic catalyst from an alkoxylated product may be utilized. If an alkali metal or alkaline earth catalyst is present, for example, a particularly advantageous method of catalyst removal involves heating the product with magnesium silicate to absorb the metal and then filtering to remove the magnesium silicate.

In a preferred embodiment of the invention, the basic catalyst is not removed from the alkoxylated glycerin tertiary alkyl partial ether but is simply neutralized by using an excess of the acidic catalyst to be utilized in the subsequent step of the process. For example, where potassium hydroxide has been employed as the basic catalyst, sufficient acidic catalyst (for example, p-toluene sulfonic acid) is added both to completely convert the potassium hydroxide to potassium p-toluene sulfonate and to provide a catalytic effect during the esterification step. The salt formed during neutralization in this manner does not interfere with the desired esterification of the alkoxylated glycerin tertiary alkyl partial ether.

In a subsequent step of the process, the alkoxylated glycerin tertiary alkyl partial ether is reacted with a fatty acid in the presence of an acidic catalyst at a temperature effective to form the esterified alkoxylated glycerin, water, and a tertiary olefin. Under certain conditions, the water and tertiary olefin co-products may be obtained in combined form as a tertiary alcohol such as tertiary butyl alcohol or tertiary amyl alcohol. Preferably, however, the temperature, pressure, and catalyst are selected such that the tertiary olefin is predominantly produced to the substantial exclusion of the tertiary alcohol. The esterification step may be carried out on a continuous, semi-continuous, or batch basis using any suitable type of reactor.

The fatty acid may be a saturated, monounsaturated, polyunsaturated straight chain or branched chain fatty acid and preferably has the general structure

wherein R is a $C_5$–$C_{23}$ olefinic or paraffinic hydrocarbon radical. Examples of suitable fatty acids include, but are not limited to, $C_6$–$C_{24}$ fatty acids such as caprylic, capric, caproic, lauric, myristic, myristoleic, stearic, palmitic, palmitoleic, rincinoleic, linoleic, linolenic, elaeostearic, elaidic, arachidic, arachindonic, behenic, erucic, oleic, and heptadecanoic acid. The fatty acids may be derived synthetically or from natural sources such as triglyceride lipids. Mixtures of fatty acid compounds, such as the mixtures of fatty acids typically obtained by hydrolysis of a triglyceride such as corn oil or soybean oil, may be advantageously used.

Sufficient fatty acid is reacted with the alkoxylated glycerin tertiary alkyl partial ether so as to place long chain fatty acid acyl groups on at least 2 and preferably all of the three "arms" or "branches" of the alkoxylated glycerin tertiary alkyl partial ether. As explained previously, operation of the process of this invention results in fatty acid acyl groups being attached directly to the glyceryl residue as well as indirectly through oxyalkylene segments. Where direct attachment is accomplished, the fatty acid acyl groups replace the tertiary alkyl groups. Where indirect attachment takes place, the fatty acid acyl groups substitute for the hydrogen of the terminal hydroxy groups of the oxyalkylene segments present in the alkoxylated glycerin tertiary alkyl partial ether intermediate. While complete conversion of both the hydroxy groups and tertiary alkyl groups is not essential, preferably at least 90% conversion of each is attained. The preferred molar ratio of fatty acid to alkoxylated glycerin tertiary alkyl partial ether is from about 3:1 to 4:1; lower ratios will result in less than complete esterification (which may be desirable for some purposes), while higher ratios are not necessary and may result in relatively large amounts of unreacted fatty acid being present in the esterified alkoxylated polyol. Since excess fatty acid must be substantially removed to render the product suitable for use as a reduced calorie fat substitute, it is beneficial to use no more than the minimum required for the desired degree of esterification.

An acidic catalyst is used which is capable of simultaneously catalyzing dissociation of the tertiary alkyl groups of the intermediate as well as esterification of the hydroxy groups. Preferably, the apparent pKa of the catalyst is less than or equal to about 1. The rate and selectivity of the desired reaction may be effectively accelerated by Lewis acids (e.g., aluminum trichloride, boron trifluoride, titanium tetrachloride), mineral acids (e.g., sulfuric acid, hydrogen halides such as hydrochloric acid, phosphoric acid, phosphorus pentoxide), organic acids (e.g., alkyl and aryl sulfonic acids, halogenated carboxylic acids), insoluble inorganic acids (e.g., acidic zeolites, heteropolyacids, acidic silicates and aluminosilicates, acidic alumina, acidic silica gel), and the like. Preferably, the acidic catalyst is relatively nonvolatile in order to facilitate removal of the water and tertiary olefin co-products generated during esterification.

In a particularly preferred embodiment of the invention, a heterogenous acidic catalyst insoluble in the esterification reaction mixture is employed. Such catalysts may be readily removed from the reaction product by filtration or other means of separating a solid from a liquid. The esterification step thus may be conveniently practiced using a fixed bed, packed bed, moving bed, or slurry type reactor. The esterification reaction mixture (exclusive of the acidic catalyst) is preferably maintained as a liquid phase. Cation exchange resins have been found to be especially appropriate for use in view of their high activity, high selectivity, stability and ease of recovery. Such resins are desirably organic polymers functionalized with strong acid groups such as sulfonic or phosphoric acid groups. Examples of suitable cation exchange resins include, but are not limited to, sulfonated styrene-divinyl benzene copolymers (as well as other resins obtainable by polymerization or copolymerization of aromatic vinyl compounds followed by sulfonation), sulfonated styrene-butadiene resins, phenol-formaldehyde sulfonic acid resins, sulfonated resinous polymers of cumerone-indene with cyclopentadiene, sulfonated coals, perfluorinated sulfonic acid-functionalized resins, and the like, which preferably are in cross-linked, macroreticular, and/or macroporous form having a surface area of from 20 to 600 square meters per gram. The degree of cross-linking is desirably controlled so as to permit diffusion of the reactants into the cation exchange resin and intimate association of the reactants with the active acidic sites. The use of high surface area resins may be advantageous in order to realize optimum conversion rates. The cation exchange resin is preferably used in a granular size of from about 0.25 to 2 mm, although smaller or larger particles or beads may also be employed. Since the reactants utilized in the present invention tend to be fairly bulky molecules, the use of cation exchange resins having relatively large pores or pore volumes may be beneficial. Preferably, the catalyst is one which is thermally stabilized such that gradual deterioration or deactivation of the resin is minimized. Varying degrees of stabilization have been attained by the incorporation of electron withdrawing groups, particularly halogens such as bromine and chlorine, into the cation exchange resin. Stabilized catalysts of this type are well known and are described in U.S. Pat. Nos. 3,256,250, 3,342,755, 4,269,943 and British Pat. No. 1,393.594, the teachings of which are incorporated herein by reference in their entirety. Numerous acidic resins suitable for use in the process of this invention are also available commercially including "Amberlyst 15" resin (available from Rohm & Haas), "Amberlyst YN-1010" resin (available from Rohm & Haas), "Dowex 50W" resin (available from Dow Chemical), "Dowex MSC-1" (available from Dow Chemical), and "Nation" resin (available from E. I. duPont deNemours).

The concentration of acidic catalyst is selected such that the desired degree of esterification of the alkoxylated glycerin tertiary alkyl partial ether is accomplished in a practically short period of time (e.g., the reaction, residence, or hold-up time may be from 15 minutes to 18 hours). While the optimum catalyst concentration will vary depending upon factors such as catalyst activity and temperature, typically from 0.001 to 25 weight percent of the acidic catalyst based on the total weight of fatty acid and alkoxylated glycerin tertiary alkyl partial ether will be sufficient.

Similarly, the temperature is chosen such that it is sufficiently high to esterify the alkoxylated glycerin tertiary alkyl partial ether at a reasonably rapid rate but not so high that generation of undesirable by-products or decomposition of the esterified alkoxylated glycerin occurs to an appreciable extent. Generally speaking, reaction temperatures of from 25° C. to 300° C. will be appropriate for use, with the temperature range of from 50° C. to 225° C. being most preferred.

In one desirable embodiment of the invention, the tertiary olefin and water co-products are removed from the esterification reaction zone (preferably, as they are formed or shortly thereafter). This may be readily accomplished by distillative means since both co-products are considerably more volatile than the other components present in the reaction mixture. Removal of the co-products may be expedited through the application of vacuum, i.e., by conducting the esterification reaction under subatmospheric (reduced) pressure. The reaction is desirably carried out under a pressure of from about 0.1 to about 200 mm Hg (preferably, from about 1 to 50 mm Hg). Sparging of an inert stripping agent such as nitrogen or a volatile hydrocarbon may also be utilized, either alone or in combination with the application of vacuum. The removal conditions are selected such that essentially only the tertiary olefin and water taken overhead; the reactants and the esterified alkoxylated polyol product are retained in the esterification reaction zone: To drive the esterification to completion, it is desirable to minimize the concentration of both co-products within the reaction zone. In general, reaction times will be shortened where the concentration of each co-product is maintained below 5% by weight (more preferably, below 1% by weight). The tertiary olefin which is removed from the reaction zone may be separated from the water and recycled for using in synthesizing additional quantities of the tertiary alkyl partial ether of glycerin needed as a starting material for the process of this invention. Suitable separation means include distillation (including evaporation) and the like.

If desired, the esterification step may be carried out in stages wherein the temperature, pressure, catalyst concentration, or rate of co-product removal is advantageously varied between stages. Multizone continuous equipment having a serial sequence of separate reaction vessels or a multi-tray column reactor with crossflow countercurrent stripping equipment could be utilized. The reactants may be combined all at once in the reaction zone or in portions. In one variation. the esterification reaction may be carried out to achieve partial conversion of the reactants prior to removal of any of the co-products from the reaction zone. For example, equilibrium or near-equilibrium between the reactants and products could be attained in a first stage, followed by the initiation of co-product removal in order to increase the yield of esterified alkoxylated polyol.

When the esterification reaction has proceeded to the extent desired, the acidic catalyst may be removed or deactivated by an appropriate method. For example, if the acidic catalyst is a soluble species, the reaction product can be contacted with a particulate absorbent such as magnesium or aluminum silicate at an appropriate temperature (typically, 50° C. to 150° C.) so as to absorb the catalyst onto the absorbent and then filtered. Alternatively, the reaction product can be treated with a base so as to neutralize the acidic catalyst. The neutralized catalyst typically forms a precipitate which can be removed by filtration. Treatment with an appropriate ion exchange resin or extraction with water or dilute aqueous base may also be utilized. In the preferred embodiment of this invention wherein a heterogeneous (insoluble) acidic catalyst such as a sulfonated ion exchange resin is employed, the catalyst may be readily separated from the reaction product by filtration, centrifugation, decantation, or other such separation means. if the acidic catalyst is developed in the form of a fixed bed, the liquid product stream withdrawn from the esterification reaction zone will be essentially free of catalyst. Periodic regeneration of the recovered acidic catalyst prior to reuse may be desirable to maintain high efficiency and selectivity.

The esterified alkoxylated polyol produced by the process of this invention can be additionally purified or treated if desired using any of the techniques known in the art for refining natural vegetable or animal oils and fats. Such techniques include, but are not limited to, degumming, bleaching, filtration, deodorization, hydrogenation, deacidification (neutralization), steam stripping, fractional crystallization, dewaxing, and the like. Various additives such as stabilizers, anti-oxidants, vitamins and so forth can also be incorporated into the esterified alkoxylated polyol.

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

The tertiary butyl monoether of glycerin is prepared by heating a mixture of glycerin (500 parts by weight), isobutylene (275 parts), and sulfuric acid (18 parts) at 75° C. for 2 hours. The mixture is cooled, neutralized and vacuum distilled at 12 mm Hg until the temperature reaches 168° C. The distillate, when redistilled at 5 mm Hg, provides the desired monoether having a boiling point of 93°–94° C.

A propoxylated glycerin tertiary butyl monoether containing about 6 equivalents of propylene oxide per equivalent of glycerin is prepared by charging the tertiary butyl monoether of glycerin (148 parts) and an aqueous solution of 45 percent potassium hydroxide (5 parts) to an autoclave equipped with temperature, pressure, and vacuum controls. The autoclave is evacuated to less than 10 mm Hg while being heated to 110° C. to remove water. The autoclave is thereafter repressurized with nitrogen to 34 psig. Propylene oxide (348 parts) is then added incrementally over a 5 hour period. The reaction mixture is held at 110° C. until at least 99% conversion of the propylene oxide is achieved (approximately 4 hours). The propoxylated glycerin tertiary butyl monoether product is thereafter heated at 110° C. for 3 hours with magnesium silicate (25 parts) and filtered to remove the potassium catalyst.

To obtain the desired esterified alkoxylated glycerin, the propoxylated glycerin tertiary butyl monoether (496 parts) is heated with soybean oil fatty acids (in sufficient quantity to provide 3 equivalents of fatty acid per equivalent of the monoether) and p-toluene sulfonic acid (10 parts) at 125° C. and 10 mm Hg pressure until at least 95% conversion of the fatty acid has been accomplished. The residual p-toluene sulfonic acid is removed by washing several times with an equal volume of water. The washed product is thereafter vacuum steam distilled by heating to 200°–205° C. under 10 mm Hg pressure with water being slowly bled below the surface of the liquid product (total amount of water added is 3 parts water per part esterified alkoxylated glycerin product). The purified product thus obtained is an esterified propoxylated monoglyceride suitable for use as a fat substitute in the preparation of reduced calorie food compositions.

EXAMPLE 2

The procedure of Example 1 is repeated, with the following changes, to obtain an esterified alkoxylated diglyceride fat substitute.

The tertiary butyl diether of glycerin is prepared by heating a mixture of glycerin (250 parts), isobutylene (400 parts), and sulfuric acid (18 g) at 75° C. for 1.5 hours. The mixture is cooled, treated with sufficient concentrated alkali solution to neutralize the acid, and vacuum distilled, the major fraction coming over at 88°–95° C. (3–4 mm Hg). This fraction is washed with an equal volume of water; the upper layer is dried with magnesium sulfate, filtered, and redistilled. The diether is collected at 80°–84° C. (4 mm Hg).

An alkoxylated glycerin tertiary butyl diether containing about 2 equivalents each of propylene oxide and ethylene oxide per equivalent of glycerin is prepared by reacting the tertiary butyl diether of glycerin (204 parts) with a mixture of ethylene oxide (88 parts) and propylene oxide (116 parts) in the presence of potassium catalyst as described in Example 1. In the esterification step, the alkoxylated glycerin tertiary butyl diether (408 parts) is reacted with a 2:1 (weight:weight) mixture of hydrogenated high erucic rapeseed oil fatty acids (a 5% stoichiometric excess of fatty acid relative to hydroxy and tertiary alkyl ether groups being employed) at 150° C. in the presence of a sulfonated styrene-divinyl benzene cation exchange resin (20% by weight based on the total amount of diether and fatty acid). The acidic catalyst is removed by filtration prior to vacuum steam distillation.

EXAMPLE 3

The procedure of Example 1 is repeated using 1,2-butene oxide (288 parts) in place of propylene oxide in the alkoxylation step and using stearic acid instead of soybean fatty acids in the esterification step.

EXAMPLE 4

The procedure of Example 1 is repeated using 166.5 parts by weight of a 2:1 (mole:mole) mixture of the tertiary amyl monoether of glycerin and the tertiary amyl diether of glycerin in place of the tertiary butyl monether of glycerin and 464 parts by weight of propylene oxide in the alkoxylation step. Coconut oil fatty acids are used as the fatty acid source while sulfuric acid (1 part by weight) is employed as the acidic catalyst (esterification temperature=90° C.).

I claim:

1. An integrated process for producing an esterified alkoxylated glycerin having one or two fatty acid acyl groups attached directly to glycerin comprising
   (a) hydrolyzing a triglyceride to form glycerin and a fatty acid;
   (b) reacting the glycerin with a $C_4$–$C_5$ tertiary olefin to form a tertiary alkyl partial ether of glycerin;
   (c) reacting the tertiary alkyl partial ether of glycerin with a $C_2$–$C_6$ aliphatic epoxide in the presence of a basic catalyst to form an alkoxylated glycerin tertiary alkyl partial ether;
   (d) reacting the alkoxylated glycerin tertiary alkyl partial ether with the fatty acid in the presence of an acidic catalyst at a temperature effective to form the esterified alkoxylated glycerin, water, and the tertiary olefin; and
   (e) recovering and recycling the tertiary olefin for use in step (b).

2. The integrated process of claim 1 wherein the triglyceride is selected from a group consisting of babasso oil, coconut oil, corn oil, cottonseed oil, olive oil, palm oil, palm kernal oil, cocoa butter, peanut oil, rapeseed oil, safflower oil, butter, lard, tallow and mixtures and hydrogenated derivatives thereof.

3. The integrated process of claim 1 wherein step (e) is accomplished by distillative means.

4. The integrated process of claim 1 wherein the $C_4$–$C_5$ tertiary olefin is isobutylene.

5. The integrated process of claim 1 wherein the molar ratio of glycerin: $C_4$–$C_5$ tertiary olefin is from 1:0.9 to 1:2.2.

6. A process for producing an esterified alkoxylated glycerin having one or two fatty acid acyl groups attached directly to glycerin comprising the steps of
   (a) reacting a tertiary butyl partial ether of glycerin with an epoxide selected from a group consisting of ethylene oxide, propylene oxide, 1,2-butene oxide and mixtures thereof in the presence of an alkali metal catalyst at a temperature of from 50° C. to 150° C. to form an alkoxylated glycerin tertiary butyl partial ether, wherein the molar ratio of epoxide: glycerin is from 1:1 to 20:1; and
   (b) reacting the alkoxylated glycerin tertiary butyl partial ether with a $C_6$–$C_{24}$ fatty acid in the presence of an acidic catalyst selected from a group consisting of Lewis acids, mineral acids, organic acids, insoluble inorganic acids, cation exchange resins and mixtures thereof at a temperature of from 25° C. to 300° C. to form the esterified alkoxylated glycerin, water, and isobutylene.

7. The process of claim 6 wherein said alkali metal catalyst is a sodium or potassium catalyst.

8. The process of claim 6 wherein the molar ratio of alkoxylated glycerin tertiary butyl partial ether: $C_6$–$C_{24}$ fatty acid is from 1:3 to 1:4.

9. The process of claim 6 wherein the acidic catalyst is a cation exchange resin and said cation exchange resin is a macroreticular sulfonated styrene-divinyl benzene cation exchange resin.

10. A process for producing an esterified alkoxylated glycerin having from one to two fatty acid acyl groups attached directly to glycerin comprising the steps of
    (a) reacting a tertiary alkyl partial ether of glycerin with a $C_2$–$C_6$ aliphatic epoxide in the presence of a basic catalyst to form an alkoxylated glycerin tertiary alkyl partial ether; and
    (b) reacting the alkoxylated glycerin tertiary alkyl partial ether with a fatty acid in the presence of an acidic catalyst at a temperature effective to form the esterified alkoxylated glycerin, water, and a tertiary olefin.

11. The process of claim 10 wherein the tertiary alkyl partial ether of glycerin has the general structure $$(HO)_x\text{—G—}(OR)_y$$

wherein x is 1 or 2, y is 1 or 2, the sum of x+y is 3, G is a glyceryl residue, and R is tertiary butyl or tertiary amyl.

12. The process of claim 10 wherein the $C_2$–$C_6$ aliphatic epoxide is selected from a group consisting of ethylene oxide, propylene oxide, 1,2-butene oxide, isobutylene oxide, 2,3-butene oxide, 1,2-pentene oxide, 2-methyl 2,3-butene oxide, cyclopentene oxide, 1,2-hexene oxide, cyclohexene oxide, methyl glycidyl ether, ethyl glycidyl ether, and mixtures thereof.

13. The process of claim 10 wherein the basic catalyst is an alkali metal catalyst.

14. The process of claim 10 wherein step (a) is performed at a temperature of from 50° C. to 150° C.

15. The process of claim 10 wherein the molar ratio of $C_2$–$C_6$ aliphatic epoxide: tertiary alkyl partial ether of glycerin is from 1:1 to 20:1.

16. The process of claim 10 wherein the fatty acid is selected from the group consisting of caprylic, undecylic, capric, lauric, caproic, myristic, myristoleic, stearic, isostearic, palmitic, palmitoleic, rincinoleic, linoleic, elaidic, linolenic, elaeostearic, arachidic, arachidonic, behenic, erucic, oleic, pentadecanoic, and heptadecanoic acid and mixtures thereof.

17. The process of claim 10 wherein the acidic catalyst is selected from a group consisting of Lewis acids, mineral acids, organic acids, insoluble inorganic acids, cation exchange resins, and mixtures thereof.

18. The process of claim 10 wherein step (b) is performed at a temperature of from 25° C. to 300° C.

19. The process of claim 10 wherein step (b) is performed in a reaction zone with said water and tertiary olefin being removed from said reaction zone during said step.

20. The process of claim 10 wherein step (b) is performed at subatmospheric pressure.

21. The process of claim 10 wherein said fatty acid is obtained by hydrolysis of a triglyceride.

* * * * *